United States Patent
Bandyopadhyay et al.

(10) Patent No.: US 9,439,846 B2
(45) Date of Patent: Sep. 13, 2016

(54) ORAL CARE COMPOSITION

(75) Inventors: Prasun Bandyopadhyay, Bangalore (IN); Gautam Banerjee, Bangalore (IN); Amit Kumar Ghosh, Bangalore (IN); Reshmee Mukhopadhyay, Bangalore (IN); Smitha Ashok Upadhyaya, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 142 days.

(21) Appl. No.: 14/125,323

(22) PCT Filed: May 15, 2012

(86) PCT No.: PCT/EP2012/059031
§ 371 (c)(1),
(2), (4) Date: Feb. 24, 2014

(87) PCT Pub. No.: WO2012/171738
PCT Pub. Date: Dec. 20, 2012

(65) Prior Publication Data
US 2014/0170084 A1    Jun. 19, 2014

(30) Foreign Application Priority Data

Jun. 17, 2011 (IN) .................... 1761/MUM/2011
Aug. 1, 2011 (EP) ..................... 11176118

(51) Int. Cl.
| | |
|---|---|
| *A61Q 11/00* | (2006.01) |
| *A61K 8/27* | (2006.01) |
| *A61K 33/30* | (2006.01) |
| *A61K 33/06* | (2006.01) |
| *A61K 33/10* | (2006.01) |
| *A61K 36/82* | (2006.01) |
| *A61K 8/97* | (2006.01) |
| *A61K 8/49* | (2006.01) |
| *A61K 8/19* | (2006.01) |

(52) U.S. Cl.
CPC .............. *A61K 8/498* (2013.01); *A61K 8/19* (2013.01); *A61K 8/27* (2013.01); *A61K 8/97* (2013.01); *A61Q 11/00* (2013.01)

(58) Field of Classification Search
USPC .......... 424/49, 58, 641, 682, 686, 687, 729
See application file for complete search history.

(56) References Cited

U.S. PATENT DOCUMENTS

| | | | |
|---|---|---|---|
| 4,853,213 A | * | 8/1989 | Thame .................... 424/58 |
| 2004/0219183 A1 | * | 11/2004 | Kostinko et al. ........... 424/423 |
| 2006/0140881 A1 | | 6/2006 | Xu et al. |
| 2006/0141072 A1 | | 6/2006 | Arvanitidou |
| 2007/0116652 A1 | * | 5/2007 | Kamath et al. .............. 424/58 |
| 2010/0008869 A1 | | 1/2010 | Takagi et al. |
| 2011/0165099 A1 | | 7/2011 | Arvanitidou et al. |

FOREIGN PATENT DOCUMENTS

| | | |
|---|---|---|
| EP | 2045248 | 4/2009 |
| GB | 2372209 A | 8/2002 |
| JP | 2009173572ABS | 8/2009 |
| JP | 2009196986ABS | 9/2009 |

OTHER PUBLICATIONS

IPRP2 in PCTEP2012059031, May 17, 2013.
Search Report in EP11176118, Jan. 10, 2012.
Written Opinion in EP11176118, Aug. 11, 2011.
Written Opinion in PCTEP2012059031, Jun. 19, 2012.
International Search Report, PCT/EP2012/059031, mailed Jun. 19, 2012, 4 pp.
European Search Report, EP 11 17 6118, dated Jan. 10, 2012, 2 pp.

* cited by examiner

*Primary Examiner* — Lezah Roberts
(74) *Attorney, Agent, or Firm* — Greenberg Traurig, LLP

(57) ABSTRACT

The present invention relates to an oral care composition comprising catechins. We have found that the catechins tend to darken the color of the chalk based toothpaste due to its oxidation which happens at the high pH of the toothpaste. Once the catechins are oxidized and darken the color of the toothpaste it is no longer available as such for providing anti-inflammatory benefits. It is an object of the invention to provide a chalk based toothpaste formulation which does not turn substantially dark due to oxidation of catechins. The present inventors while working with oral care compositions comprising catechins preferably green tea catechins for providing anti-inflammatory benefits, surprisingly found that some selected zinc salts when added in particular quantities do not result in darkening the color of the toothpaste, and also, when stored, are able to deliver green tea catechins.

12 Claims, No Drawings

ORAL CARE COMPOSITION

FIELD OF THE INVENTION

The present invention relates to an oral care composition more particularly the present invention relates to an oral care composition comprising catechins.

BACKGROUND OF THE INVENTION

Oral care and oral hygiene is one of the most important things in a human's life. Everyday most people brush their teeth to keep themselves orally hygienic. Most people brush their teeth at least twice each day and sometimes even more than that. On the other hand due to lack of proper dental care a number of people suffer from inflammation in their gums which causes irritations and problems in their mouth.

Most commonly known oral care composition is toothpaste. People throughout the world use toothpaste for their oral health and hygiene. Toothpastes are available in many formats. The most common format is chalk based toothpaste formulations.

Efforts have been made to incorporate different plant extract and/or antibacterial agents in toothpaste compositions to fight against oral inflammation.

US2006/0140881 (COLGATE-PALMOLIVE COMPANY, 2006) discloses an oral care composition containing: a free-B-ring flavonoid and a flavan; as well as at least one bioavailability-enhancing agent. Methods of using the oral compositions are also provided.

US2006/0141072 (COLGATE-PALMOLIVE COMPANY, 2006) discloses low water tooth pastes which contain a variety of plant extracts. The oral or dentifrice compositions contain humectants, abrasive compounds, and a variety of plant extracts, such as rosemary and green tea extracts, along with an additional antioxidant component. Examples of antioxidants include stannous compounds, sodium metabisulfite, BHT, ammonium sulfate, and potassium stannate. The compositions are resistant to browning. The invention also provides methods for promoting the oral health of a subject animal comprising applying a composition as discussed above to the oral surfaces of the animal.

Catechins in general are known for their health benefits. In the world of tea, green tea is also well known for its health benefits. Green Tea catechins including Epigallocatechin, Epigallocatechin gallate etc are known to provide anti-inflammatory benefits. We have found that the catechins in general, such as those present in the green tea tend to darken the colour of the chalk based toothpaste due to its oxidation which happens at the high pH of the toothpaste. Once the catechins are oxidized and darken the colour of the toothpaste they are no longer available as such for providing anti-inflammatory benefits.

Therefore there is a need to develop an oral care composition which will use the benefits of catechins in a chalk based toothpaste formulation without substantially darkening the colour of the toothpaste.

OBJECTS OF THE INVENTION

In view of the foregoing, it is an object of the present invention to provide an oral care composition comprising catechins.

It is another object of the present invention to provide an oral care composition which uses the anti-inflammatory benefits of catechins.

It is a further object of the invention to provide a chalk based toothpaste formulation which does not turn substantially dark due to oxidation of catechins.

It is yet another object of the present invention to provide a chalk based toothpaste formulation with green tea catechins which does not turn substantially dark due to oxidation of green tea catechins The present inventors while working with oral care compositions comprising catechins preferably green tea catechins for providing anti-inflammatory benefits, surprisingly found that some selected zinc salts when added in particular quantities do not results in darkening the colour of the toothpaste and also when stored are able to deliver green tea catechins.

SUMMARY OF THE INVENTION

According to a first aspect of the present invention there is provided an oral care composition comprising:
a) 0.1 to 5% by weight of one or more catechins;
b) 0.1 to 10% by weight of a zinc salt selected from zinc chloride, zinc nitrate and zinc acetate or mixtures thereof; and
c) an orally acceptable base comprising calcium carbonate.

According to a second aspect the present invention provides the use of an oral care composition of the first aspect for anti-inflammatory benefit.

According to a third aspect the present invention provides the use of a zinc salt selected from zinc chloride, zinc nitrate and zinc acetate or mixtures thereof to stabilize catechins in an oral care composition comprising calcium carbonate.

According to a preferred aspect the present invention provides an oral care composition of the first aspect wherein the source of catechins is a green tea extract.

These and other aspects, features and advantages will become apparent to those of ordinary skill in the art from a reading of the following detailed description. For the avoidance of doubt, any feature of one aspect of the present invention may be utilised in any other aspect of the invention. It is noted that the figures given in the description below are intended to clarify the invention and are not intended to limit the invention to those figures per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The present invention provides an oral care composition comprising:
a) 0.1 to 5% by weight of one or more catechins;
b) 0.1 to 10% by weight of a zinc salt selected from zinc chloride, zinc nitrate and zinc acetate or mixtures thereof; and
c) an orally acceptable base comprising calcium carbonate.

The oral care composition of the invention comprises 0.1 to 5% by weight of one or more catechins. More preferably the oral care composition comprises 1 to 4% by weight of one or more catechins. The preferred source of catechins is a green tea extract. The oral care composition of the present invention preferably comprises 1 to 5% of green tea extract and more preferably comprises 1 to 4% of green tea extract. Green tea extract is a preferred source of catechins, but the oral care composition is not limited to only green tea catechins. Any other suitable source of catechins may also be preferably used.

Green tea is well known in the world of teas. Generally green tea is produced by steaming or pan-firing tea leaves immediately after plucking, so that enzyme action is inhibited and endogenous components in the leaves are retained in the product mainly unchanged. Therefore, the taste is primarily determined by the choice of clone, time of the plucking, shoot maturity and the cultivation method. Major constituents of green tea polyphenols are (-) epicatechin, (-) epigallocatechin, (-) epicatechingallate and epigallocatechin gallate (EGCG).

The composition of the present invention preferably comprises green tea extract. The green tea extract is from *Camellia sinensis* var. *sinensis* and/or *Camellia sinensis* var. *assamica*. The green tea extract is made preferably by extracting commercially available green tea in hot water. Hot water preferably means water at a temperature of 40 to 100° C. Alternatively commercially available green tea extract in power form may also preferably be used directly for making the oral care formulation. The green tea is preferably fine granulated and comprises Gallic acid, catechins and their derivatives viz. Gallic acid, EGC, ECG, EGCG, Caffeine, and Catechins. The typical EGCG content in these powders ranges from 25-40% whereas the total polyphenols content varies from 45 to 70% by dry weight. In the more preferable green tea powder the EGCG content is in the range of 30 to 35% by dry weight.

Alternatively instead of green tea extract, purified green tea catechins may be used.

The green tea extract preferably used for making the oral care formulation of the present invention preferably comprises 20 to 80% of catechins more preferably 40 to 60% of catechins by dry weight basis.

The oral care composition of the present invention also comprises a zinc salt. The zinc salt is selected from zinc chloride, zinc nitrate and zinc acetate. Alternatively a mixture of two or more of these zinc salts may be used in the formulation.

The amount of zinc salt is in the range of 0.1 to 10% by weight of the oral care composition of the invention. The preferable range for the zinc salt is in between 1 to 8% and more preferably from 1 to 5% by weight of the oral care composition.

The orally acceptable base means a base formulation which is capable of application in human mouth. The oral care composition of the invention comprises calcium carbonate. Any form of calcium carbonate may be used for the oral care composition but the most preferable form of calcium carbonate is finely ground natural chalk (FGNC). The preferred amount of calcium carbonate in the oral care composition of the invention is in the range of 20 to 80% by weight of the oral care composition. The most preferred range is in between 30 to 60% weight of the oral care composition.

The oral care compositions of the present invention may furthermore comprise optional ingredients such as pharmaceutically acceptable carriers like starch, sucrose, water or water/alcohol systems etc. Small amounts of surfactants may also be included, such as anionic, nonionic and amphoteric surfactants.

The oral care compositions may comprise particulate abrasive materials such as silicas, aluminas, dicalciumphosphates, calcium pyrophosphates hydroxyapatites, trimetaphosphates, insoluble hexametaphosphates, and agglomerated particulate abrasive materials and so on, usually in amounts between 5 and 60% by weight.

Furthermore, the oral care formulations may comprise humectants such as glycerol, sorbitol, propyleneglycol, xylitol, lactitol and so on.

Binders and thickeners such as sodium carboxymethylcellulose, xanthan gum, gum arabic etc. may also be included, as well as synthetic polymers such as polyacrylates and carboxyvinyl polymers such as Carbopol®.

Flavours, such as peppermint and spearmint oils may also be included, as well as preservatives, pH-adjusting agents, sweetening agents and so on.

Anti-bacterial agents may also be included such as Triclosan, chlorhexidine, copper. Further examples of anti-bacterial agents are quaternary ammonium compounds such as cetylpyridinium chloride; bis-guanides such as chlorhexidine digluconate, hexetidine, octenidine, alexidine; halogenated bisphenolic compounds such as 2,2' methylenebis-(4-chloro-6-bromophenol). Polymeric compounds which can enhance the delivery of anti-bacterial agents can also be included.

Anti-caries agents such as sodium- and stannous fluoride, aminefluorides, monosodiumfluorophosphate, casein, plaque buffers such as urea, calcium lactate, calcium glycerophosphate, and strontium polyacrylates may also be included. Other optional ingredients include vitamins such as Vitamin C. Desensitising agents such as potassium citrate, potassium chloride, potassium tartrate, potassium bicarbonate, potassium oxalate, potassium nitrate as well as strontium salts may also be included.

Buffers and salts to buffer the pH and ionic strength of the compositions may also be included. The pH of the compositions usually ranges from 5-10, preferably 6-9 and especially preferably 7-8.5.

Furthermore, the oral compositions may comprise anticalculus agents such as alkalimetal pyrophosphates, hypophosphite-containing polymers, organic phosphonates, phosphocitrates etc.

In addition, the compositions may comprise functional biomolecules such as bacteriocins, antibodies, enzymes and so on.

Other optional ingredients that may be included are e.g. effervescing systems such as sodium bicarbonate/citric acid systems.

The oral care composition of the invention preferably is in the form of toothpaste. The preferred colour of the toothpaste is white.

The present invention provides the use of the oral care composition of the invention for anti-inflammatory benefit. The oral care composition of the invention may be used for use anti-inflammatory benefit.

The present invention also provides the use of a zinc salt selected from zinc chloride, zinc nitrate and zinc acetate or mixtures thereof to stabilize catechins in an oral care composition comprising calcium carbonate.

Now the invention will be demonstrated with the help of examples. The following examples are for illustration only and in no way limit the scope of the invention.

EXAMPLES

HPLC Method for the Measurement of EGCG in the Toothpaste Formulation 250 mg of the tooth paste formulation was mixed with 5 mL of distilled water. Then the mixture was sonicated for 15 minute in a sonicator bath. Then, 0.1 ml of concentrate HCl (hydrochloric acid) was added and again the content was sonicated for 15 minutes. After that 5 ml of HPLC grade methanol was added to it followed by 15 minutes sonication. Then the content was centrifuged at ~12000 rpm (G-force (g) ~3225) for 15 minutes and supernatant of that was used for HPLC injection.

EGCG in the toothpaste formulation was measured using HPLC (High Performance Liquid chromatography), using ISO 14502-2:2005(E) method. Details are as given below.

HPLC Conditions:
Instrument: Agilent HPLC (1100 Series)
Column: Phenomenex Luna Phenyl hexyl 5☐, 250×4.60 mm fitted with a C18 security guard cartridge from Phenomenex.
Mobile Phases: A—9% (volume fraction) acetonitrile, 2% (volume fraction) acetic acid with 20 microgram/mL EDTA.
  B—80% (volume fraction) acetonitrile, 2% (volume fraction) acetic acid with 20 microgram/mL EDTA.
Flow rate: 1 ml/min
Column temperature: 35° C.
Detector: Diode array detector & detection wavelength 278 nm For this analysis, caffeine is used as a standard and as described in ISO 14502-2:2005(E) method. Relative Response Factor (RRF) of EGCG with respect to Caffeine was used for EGCG quantification in the samples.

Preparation of the Oral Care Composition:

The toothpaste compositions were made according to the following Table 1. In the table there are mentioned six compositions in the examples viz. A, B, C, 1, 2 and 3. The composition as mentioned in Example A was made without any zinc salt. The compositions according to the Examples B, C, 1, 2 and 3 were made with zinc sulphate, zinc citrate, zinc acetate, zinc chloride and zinc nitrate respectively.

The following procedure was followed for making the compositions according to Table 1.

Sodium Carboxymethyl cellulose (SCMC) was added into water and then the solution was stirred for 15 minutes in a mixer to confirm its complete solubilisation. Then Sodium nitrate, Saccharin and 70% sorbitol solution was added one after another followed by mixing. The mixing was performed after addition of each ingredient. After that Sodium lauryl sulfate (SLS) was added to it and mixed well till it dissolved completely. Then Fine ground natural Chalk (FGNC), silica (trade name—Mfil®, supplier—Madhu silica pvt. Ltd., India), Sodium silicate and Sodium monofluorophosphate (SMFP) were added one after another and mixed well to confirm the homogeneity of the paste. This was followed by addition of Green tea extract powder (Trade name—Sunphenone® having EGCG content ~31% by dry weight, Supplier—Taiyo Green Power Co Ltd., Japan) and mixing it for 5 minutes.

In case of the toothpaste formulations with a zinc salt i.e. examples B, C, 1, 2 and 3, the zinc salt was added just before the addition of green tea powder.

TABLE 1

| | Compositions | | | | | |
|---|---|---|---|---|---|---|
| Ingredients (g) | Ex. A | Ex. B | Ex. C | Ex. 1 | Ex. 2 | Ex. 3 |
| Water | 28.79 | 28.79 | 28.79 | 28.79 | 28.79 | 28.79 |
| Sodium Nitrate | 0.50 | 0.50 | 0.50 | 0.50 | 0.50 | 0.50 |
| Saccharin | 0.25 | 0.25 | 0.25 | 0.25 | 0.25 | 0.25 |
| Sorbitol (70% solution) | 15.00 | 15.00 | 15.00 | 15.00 | 15.00 | 15.00 |
| FGNC | 43.30 | 41.30 | 41.30 | 41.30 | 41.30 | 41.30 |
| SCMC | 0.62 | 0.62 | 0.62 | 0.62 | 0.62 | 0.62 |
| Mfil | 3.17 | 3.17 | 3.17 | 3.17 | 3.17 | 3.17 |
| SLS | 2.50 | 2.50 | 2.50 | 2.50 | 2.50 | 2.50 |
| Green tea extract | 3.00 | 3.00 | 3.00 | 3.00 | 3.00 | 3.00 |
| Na-Silicate (30% solution) | 1.75 | 1.75 | 1.75 | 1.75 | 1.75 | 1.75 |
| SMFP | 1.12 | 1.12 | 1.12 | 1.12 | 1.12 | 1.12 |
| Zinc Salt | 0 | 2 | 2 | 2 | 2 | 2 |

Comparison of EGCG Stabilization and Discolouration:

The compositions as made according to Table 1 were tested for the EGCG content in them and also for appearance.

All the compositions (examples number A, B, C, 1, 2 and 3) were made according to the procedure disclosed herein above. The compositions were then stored for 4 weeks in a hot and humid chamber (Temperature: 45±5° C. and Relative Humidity: 77±5). After 4 weeks the compositions were taken out from the hot and humid chamber and then measured for the percentage of remaining EGCG in the compositions according the method described above. The colour of the compositions was also observed. The colour of the compositions was compared on a rating scale of 0 to 5 where '0' means the dark brown colour of the chalk based toothpaste which have green tea but does not have zinc salt (example A, after 4 weeks) and '5' means white colour of the regular chalk based toothpaste formulation without any green tea. The results are summarized in the following Table:

TABLE 2

| Parameter Measured/ Observed | Composition Number | | | | | |
|---|---|---|---|---|---|---|
| | A | B | C | 1 | 2 | 3 |
| % of remaining EGCG | 23 | 30 | 29 | 43 | 48 | 45 |
| Colour of the toothpaste as appeared | Dark Brown | Light Brown | Light Brown | Grayish white | Grayish white | Grayish white |
| Colour ratings of the toothpaste | 0 | 1 | 1 | 3 | 3 | 3 |

From Table 2, it is evident that the compositions prepared according to example numbers 1, 2 and 3 (with zinc acetate, zinc chloride and zinc nitrate respectively) have much higher percentages of EGCG remaining after 4 weeks (kept under hot and humid condition as described herein above) than those compositions prepared according to example numbers A B and C (which are with no zinc salt, zinc sulphate and zinc citrate respectively). The colour of the composition after 4 weeks is also much better for example numbers 1, 2 and 3.

Therefore by way of the present invention it is indeed possible to make a toothpaste composition with green tea catechins which can deliver an improved amount of catechins without substantially darkening the colour of the toothpaste.

The invention claimed is:

1. An oral care composition comprising:
   a) 0.1 to 4% by weight of at least one catechin, wherein the at least one catechin is epigallocatechin gallate (EGCG);
   b) 0.1 to 10% by weight of a zinc salt selected from zinc chloride, zinc nitrate and zinc acetate or mixtures thereof; and
   c) an orally acceptable base comprising calcium carbonate;
   wherein the oral care composition has a sufficient amount of the zinc salt to result in a colour rating of 3 and a higher percentage of the EGCG in the oral care composition, as compared to the same oral care composition not containing the zinc salt, when the oral care composition has been stored for four weeks at a temperature of 40-50 degrees Celsius and a relative humidity of 72-82.

2. The oral care composition as claimed in claim 1, wherein the source of the EGCG is a green tea extract.

3. The oral care composition as claimed in claim 2, comprises 1 to 5% by weight of the green tea extract.

4. The oral care composition as claimed in claim 1, wherein the green tea extract is a water extract.

5. The oral care composition as claimed in claim 4, wherein the green tea water extract is in the form of a powder.

6. The oral care composition as claimed in claim 1, further comprising 1.5 to 8% by weight of the zinc salt.

7. The oral care composition as claimed in claim 1, wherein a pH of the composition is between 5 to 10.

8. The oral care composition as claimed in claim 1, wherein the composition is in the form of a toothpaste.

9. The oral care composition as claimed in claim 1, wherein the source of calcium carbonate is finely ground natural chalk (FGNC).

10. The oral care composition as claimed in claim 9, wherein an amount of finely ground natural chalk (FGNC) is in the range of 20 to 80% by weight of the composition.

11. The oral care composition as claimed in claim 1, wherein the composition is designed to have a sufficient anti-inflammatory benefit.

12. A method, comprising:
    obtaining an oral care composition comprising:
        calcium carbonate,
        at least one catechin, wherein the at least one catechin is epigallocatechin gallate (EGCG); and
    adding a sufficient amount of a zinc salt selected from zinc chloride, zinc nitrate and zinc acetate or mixtures thereof to the oral care composition so that the oral care composition has a sufficient amount of the zinc salt to result in a colour rating of 3 and a higher percentage of the EGCG in the oral care composition, as compared to the same oral care composition not containing the zinc salt, when the oral care composition has been stored for four weeks at a temperature of 40-50 degrees Celsius and a relative humidity of 72-82.

* * * * *